(12) United States Patent
Cowan, Jr. et al.

(10) Patent No.: US 9,730,804 B2
(45) Date of Patent: Aug. 15, 2017

(54) LOCKING SPINAL FUSION DEVICE

(75) Inventors: John A. Cowan, Jr., Rome, GA (US);
D. Hal Silcox, Atlanta, GA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 891 days.

(21) Appl. No.: 13/383,667

(22) PCT Filed: May 5, 2010

(86) PCT No.: PCT/US2010/033677
§ 371 (c)(1),
(2), (4) Date: Jun. 18, 2012

(87) PCT Pub. No.: WO2011/028306
PCT Pub. Date: Mar. 10, 2011

(65) Prior Publication Data
US 2012/0245690 A1  Sep. 27, 2012

Related U.S. Application Data

(60) Provisional application No. 61/240,239, filed on Sep. 6, 2009.

(51) Int. Cl.
*A61F 2/44*  (2006.01)
*A61F 2/46*  (2006.01)
(Continued)

(52) U.S. Cl.
CPC ............ *A61F 2/447* (2013.01); *A61F 2/4465* (2013.01); *A61F 2/4611* (2013.01); *A61B 17/8042* (2013.01); *A61B 17/8665* (2013.01); *A61F 2002/2835* (2013.01); *A61F 2002/3082* (2013.01); *A61F 2002/30434* (2013.01); *A61F 2002/30438* (2013.01); *A61F 2002/30578* (2013.01); *A61F 2002/30604* (2013.01); *A61F 2002/30736* (2013.01); *A61F 2002/30774* (2013.01); *A61F 2002/30841* (2013.01); *A61F 2002/30904* (2013.01); *A61F 2220/0041* (2013.01); *A61F 2310/00011* (2013.01)

(58) Field of Classification Search
CPC .......................................... A61F 2/4455–2/447
USPC ............................................. 623/17.11, 17.16
See application file for complete search history.

(56) References Cited

U.S. PATENT DOCUMENTS

| 4,599,086 A | 7/1986 | Doty |
| 4,955,908 A | 9/1990 | Frey et al. |

(Continued)

*Primary Examiner* — Nicholas Plionis

(57) ABSTRACT

A spinal fusion device for implantation between spinal vertebrae includes an implant member having an opposed upper and lower surface, an outer sidewall having an aperture having internal threads, and an inner sidewall defining a central opening. A plate member is attached to the implant member such that the plate member is perpendicular relative to the implant member and includes a plurality of angled apertures for receiving anchoring fasteners and a central aperture for receiving a locking fastener. A locking member is attached to the cage member. The locking member includes a tubular shaft having internal threads that is inserted through the aperture of the outer sidewall of the implant member. A locking fastener is inserted through the central aperture of the plate member and into the locking member to thereby lock the spinal fusion device in position.

28 Claims, 14 Drawing Sheets

(51) Int. Cl.
*A61B 17/80* (2006.01)
*A61B 17/86* (2006.01)
*A61F 2/28* (2006.01)
*A61F 2/30* (2006.01)

(56) References Cited

U.S. PATENT DOCUMENTS

| | | | |
|---|---|---|---|
| 5,290,312 A | 3/1994 | Kojimoto et al. | |
| 5,397,364 A | 3/1995 | Kozak et al. | |
| 5,514,180 A | 5/1996 | Heggeness et al. | |
| 5,888,223 A | 3/1999 | Bray, Jr. | |
| 5,916,267 A | 6/1999 | Tienboon | |
| 6,066,175 A | 5/2000 | Henderson et al. | |
| 6,106,557 A | 8/2000 | Robioneck et al. | |
| 6,156,037 A | 12/2000 | LeHuec et al. | |
| 6,159,211 A | 12/2000 | Boriani et al. | |
| 6,235,059 B1 | 5/2001 | Benezech et al. | |
| 6,342,074 B1 | 1/2002 | Simpson | |
| 6,432,106 B1 | 8/2002 | Fraser | |
| 6,461,359 B1 | 10/2002 | Tribus et al. | |
| 6,558,387 B2 | 5/2003 | Errico et al. | |
| 6,575,972 B1 * | 6/2003 | Gordon | A61B 17/6466 606/54 |
| 6,576,017 B2 | 6/2003 | Foley et al. | |
| 6,579,290 B1 | 6/2003 | Hardcastle et al. | |
| 6,629,998 B1 | 10/2003 | Lin | |
| 6,635,087 B2 | 10/2003 | Angelucci et al. | |
| 6,682,561 B2 | 1/2004 | Songer et al. | |
| 6,706,043 B2 | 3/2004 | Steiner et al. | |
| 6,716,247 B2 | 4/2004 | Michelson | |
| 6,733,531 B1 | 5/2004 | Trieu | |
| 6,770,096 B2 | 8/2004 | Bolger et al. | |
| 6,843,804 B2 | 1/2005 | Bryan | |
| 6,926,737 B2 | 8/2005 | Jackson | |
| 6,974,479 B2 | 12/2005 | Trieu | |
| 6,984,234 B2 | 1/2006 | Bray | |
| 7,077,864 B2 | 7/2006 | Byrd, III et al. | |
| 7,112,222 B2 | 9/2006 | Fraser et al. | |
| 7,135,024 B2 | 11/2006 | Cook et al. | |
| 7,135,043 B2 | 11/2006 | Nakahara et al. | |
| 7,163,561 B2 * | 1/2007 | Michelson | A61F 2/442 606/307 |
| 7,172,627 B2 | 2/2007 | Fiere et al. | |
| 7,229,441 B2 | 6/2007 | Trieu et al. | |
| 7,232,464 B2 | 6/2007 | Mathieu et al. | |
| 7,238,203 B2 | 7/2007 | Bagga et al. | |
| 7,255,698 B2 * | 8/2007 | Michelson | A61B 17/025 606/247 |
| 7,320,708 B1 | 1/2008 | Bernstein | |
| 7,326,248 B2 | 2/2008 | Michelson | |
| 7,338,525 B2 | 3/2008 | Ferree | |
| 7,344,539 B2 | 3/2008 | Serhan et al. | |
| 7,354,452 B2 | 4/2008 | Foley | |
| 2002/0010511 A1 | 1/2002 | Michelson | |
| 2003/0083747 A1 * | 5/2003 | Winterbottom | A61F 2/28 623/17.11 |
| 2005/0027293 A1 * | 2/2005 | LeHuec | A61B 17/1671 623/17.11 |
| 2005/0033433 A1 * | 2/2005 | Michelson | 623/17.11 |
| 2005/0085913 A1 * | 4/2005 | Fraser | A61B 17/7059 623/17.11 |
| 2005/0096657 A1 * | 5/2005 | Autericque | A61B 17/7059 623/17.11 |
| 2005/0101960 A1 * | 5/2005 | Fiere | A61B 17/7059 623/17.11 |
| 2005/0171606 A1 | 8/2005 | Michelson | |
| 2005/0187628 A1 | 8/2005 | Michelson | |
| 2006/0079961 A1 | 4/2006 | Michelson | |
| 2006/0085071 A1 | 4/2006 | Lechmann et al. | |
| 2006/0206208 A1 | 9/2006 | Michelson | |
| 2007/0106388 A1 | 5/2007 | Michelson | |
| 2007/0270965 A1 | 11/2007 | Ferguson | |
| 2008/0015694 A1 * | 1/2008 | Tribus | A61B 17/1757 623/17.11 |
| 2008/0051890 A1 | 2/2008 | Waugh et al. | |
| 2008/0300634 A1 * | 12/2008 | Gray | A61B 17/7059 606/280 |
| 2009/0054987 A1 | 2/2009 | Chin et al. | |
| 2010/0305704 A1 * | 12/2010 | Messerli | A61F 2/442 623/17.16 |

* cited by examiner

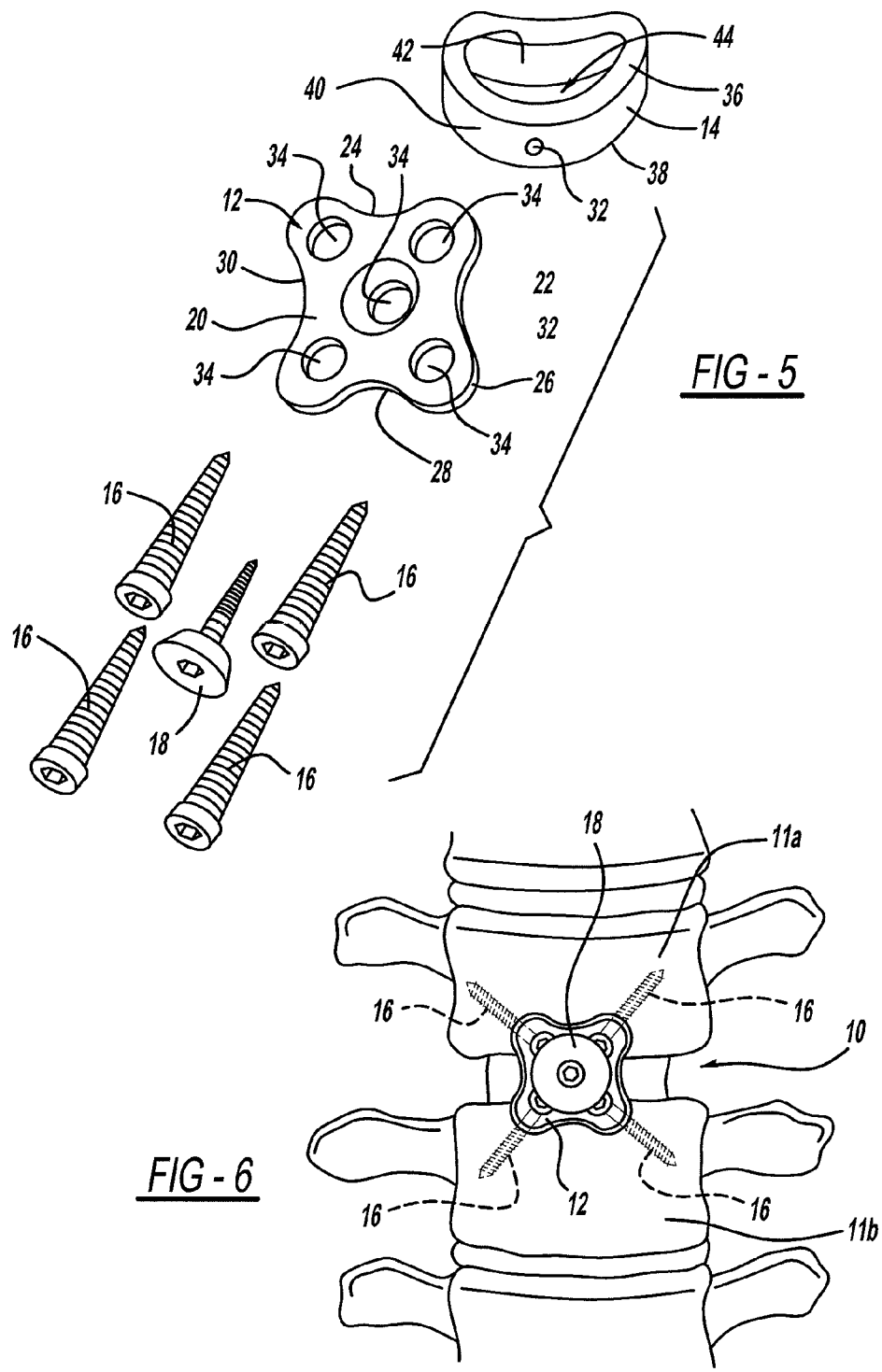

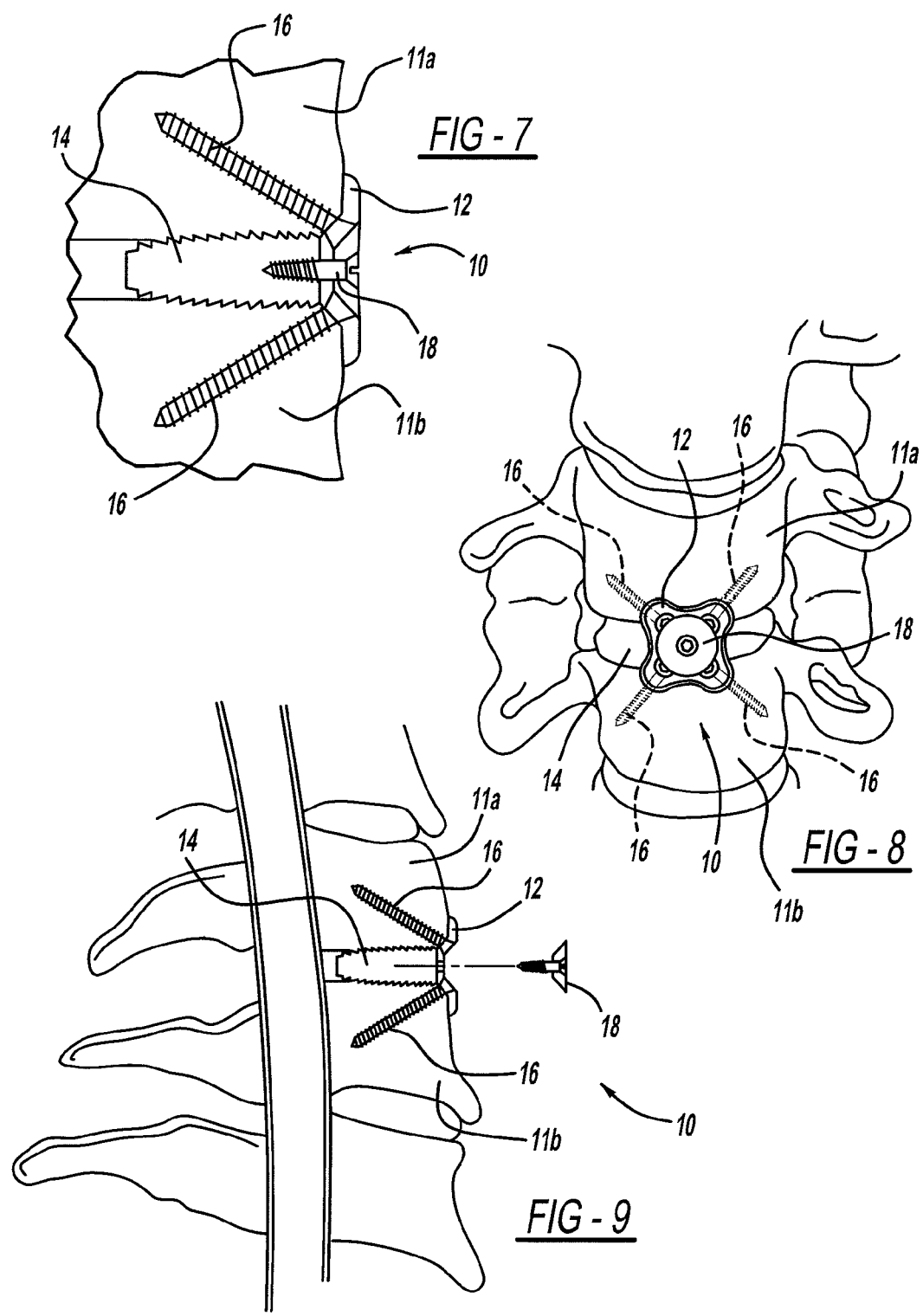

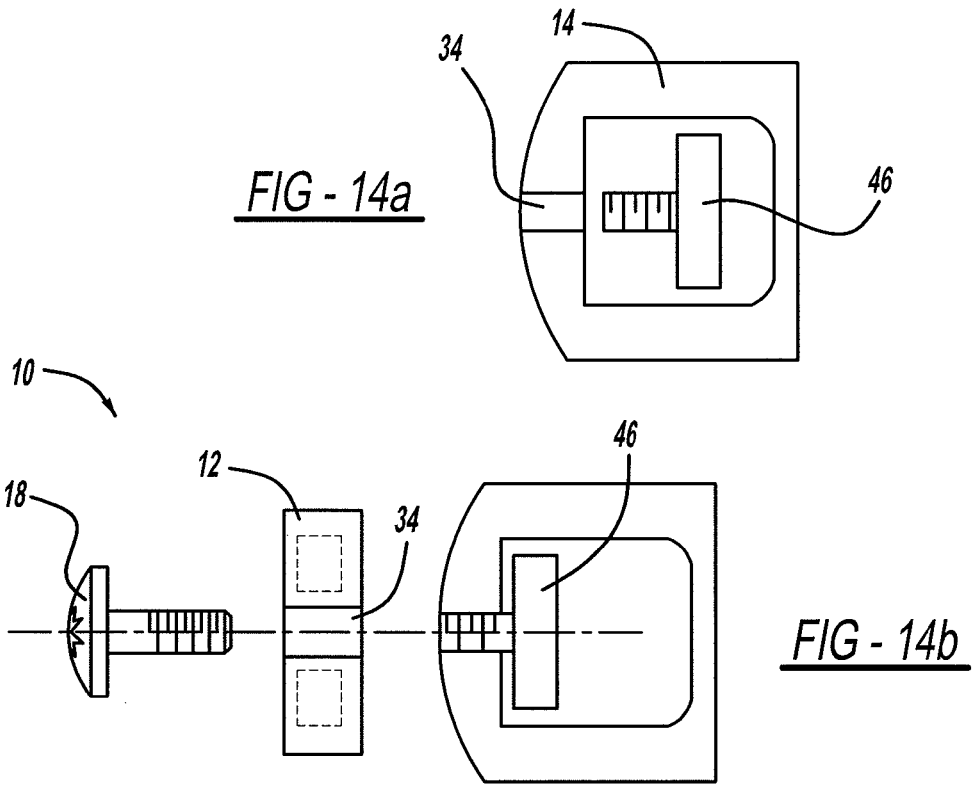
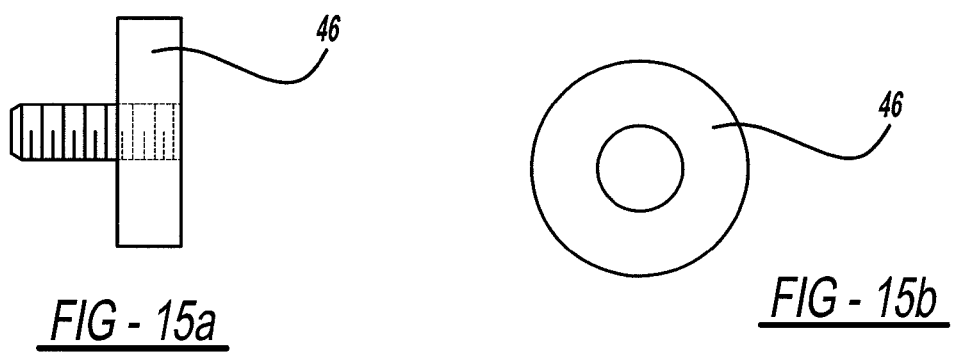
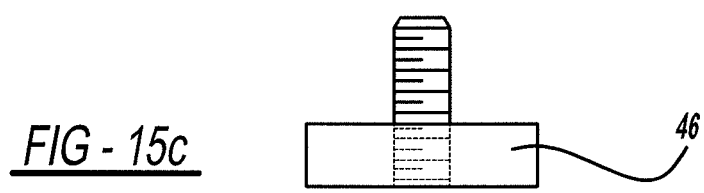

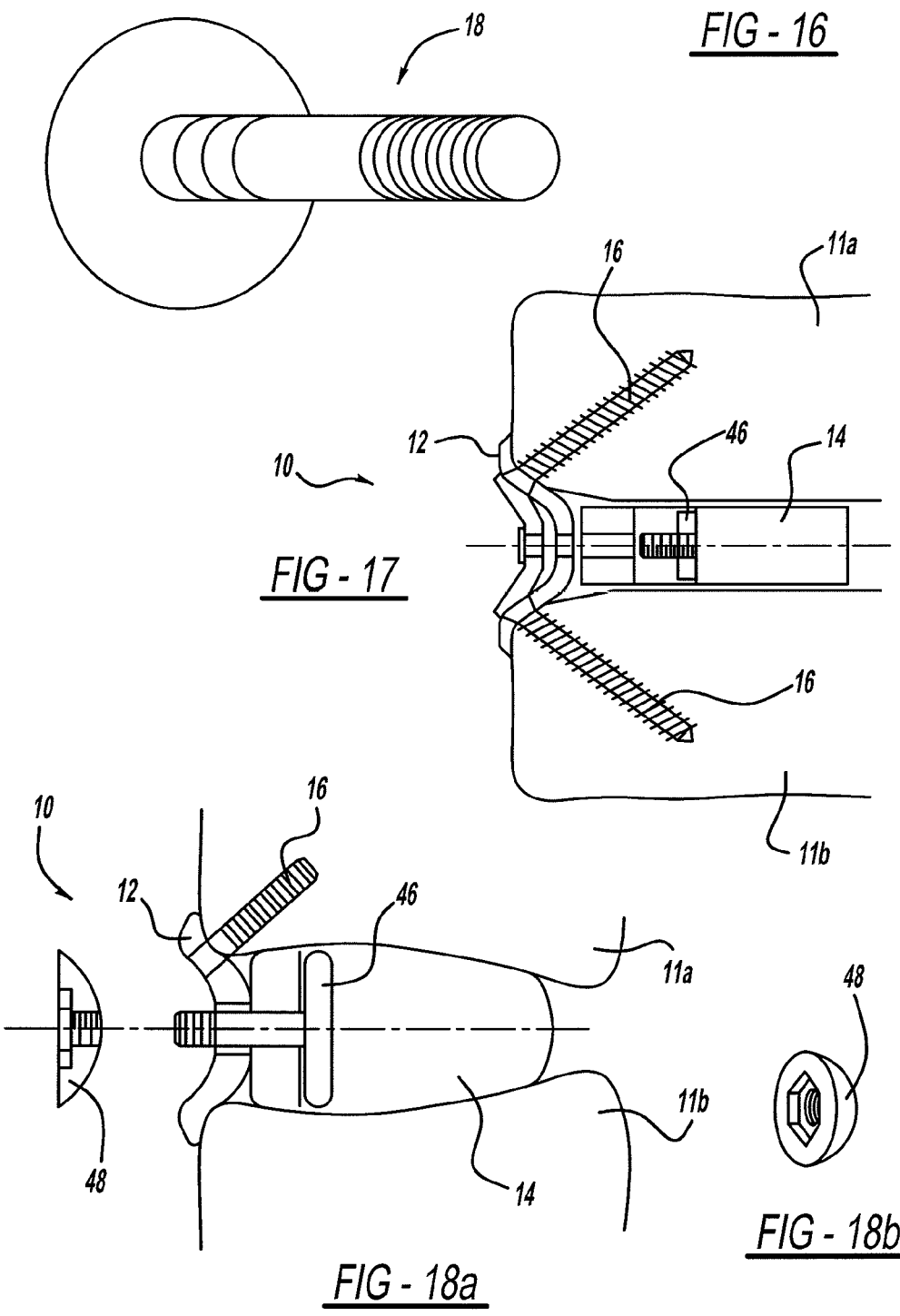

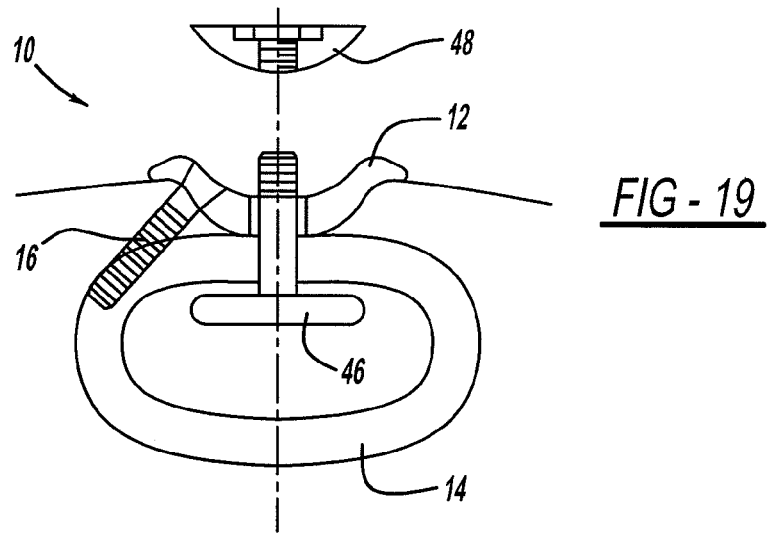
FIG - 19
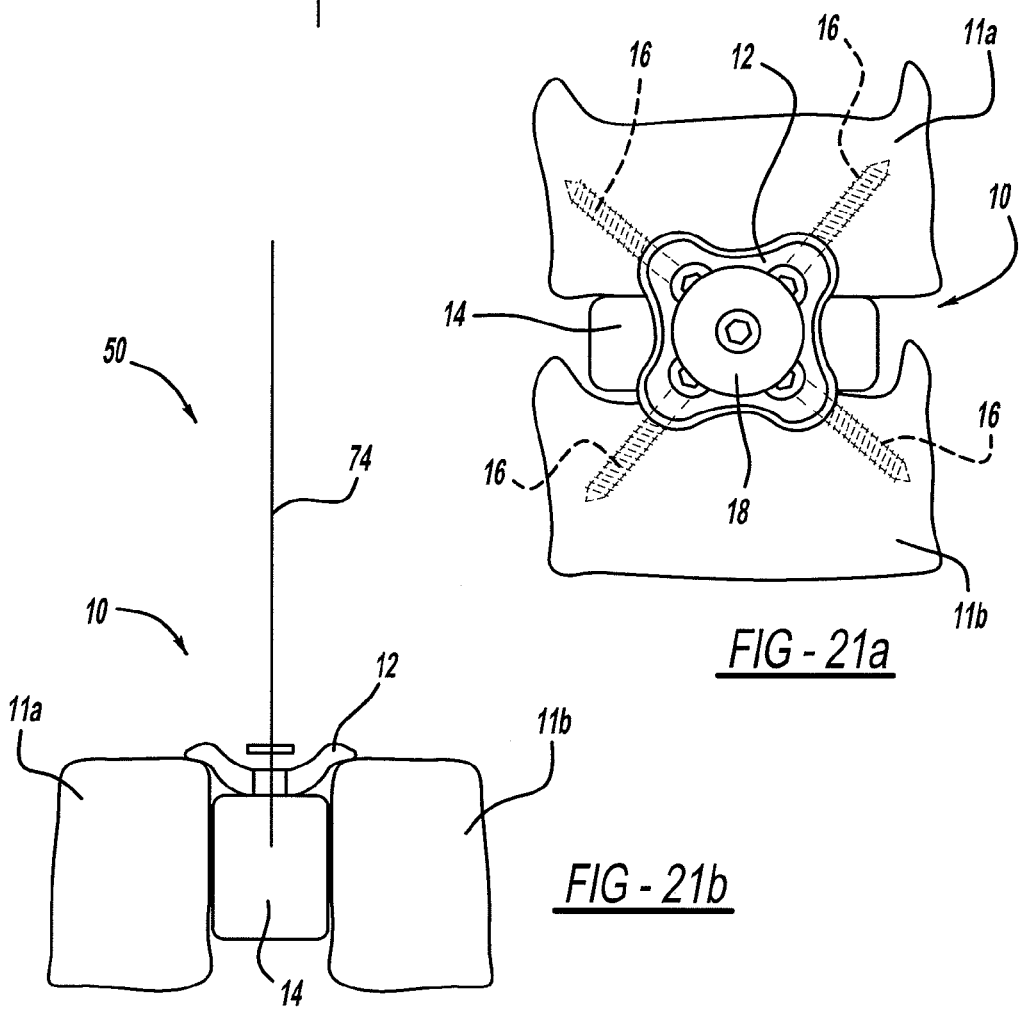
FIG - 21a
FIG - 21b

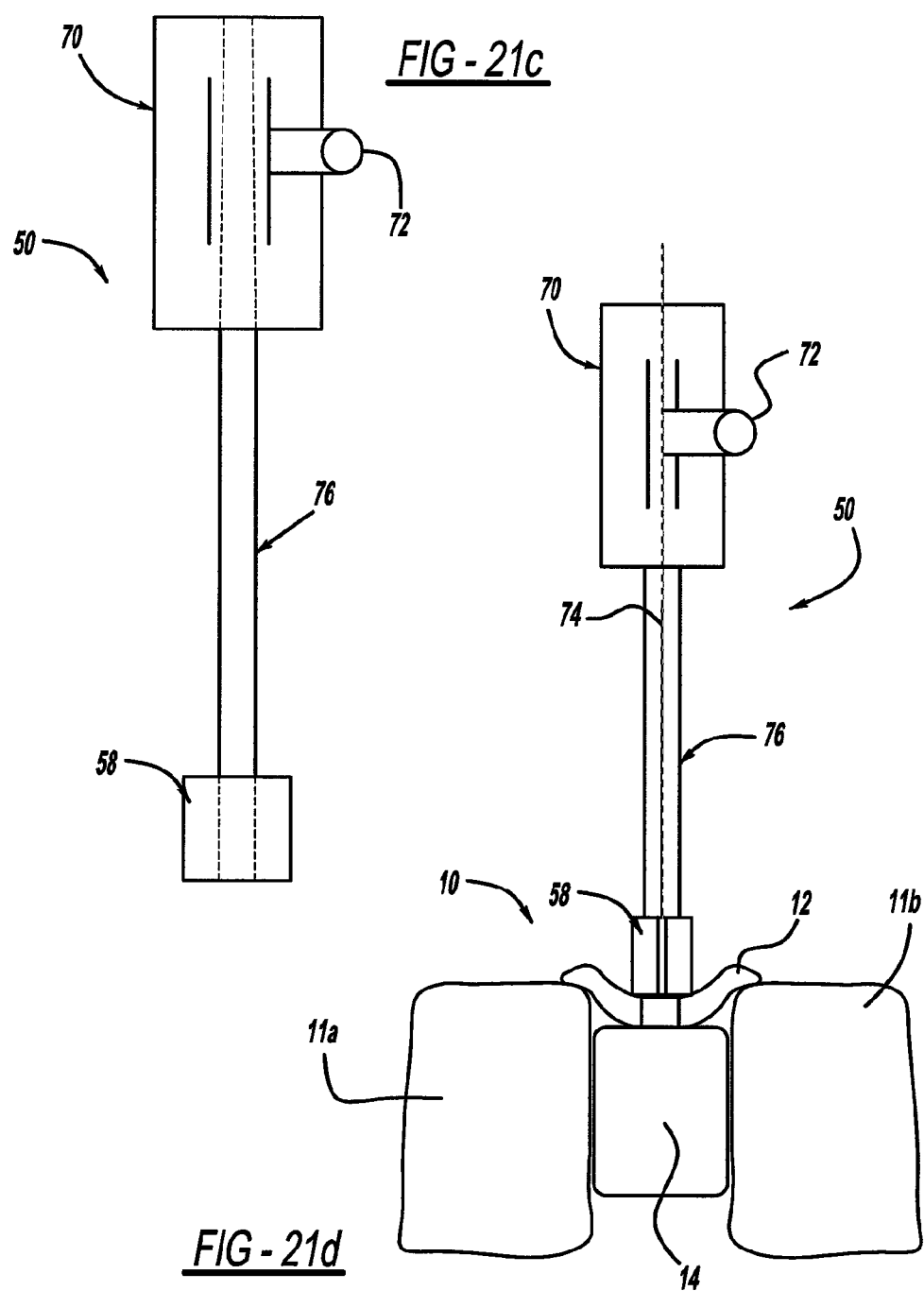

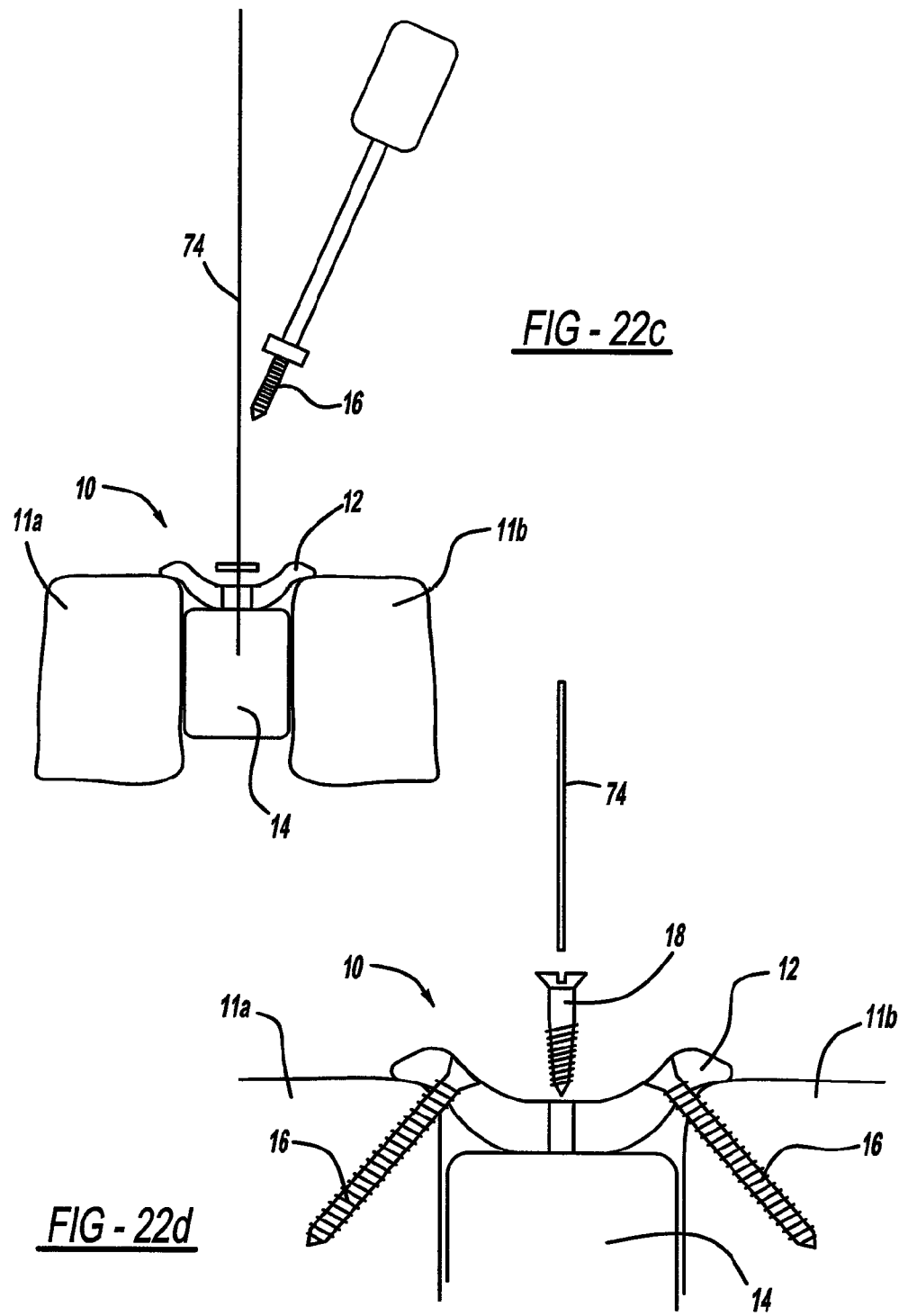

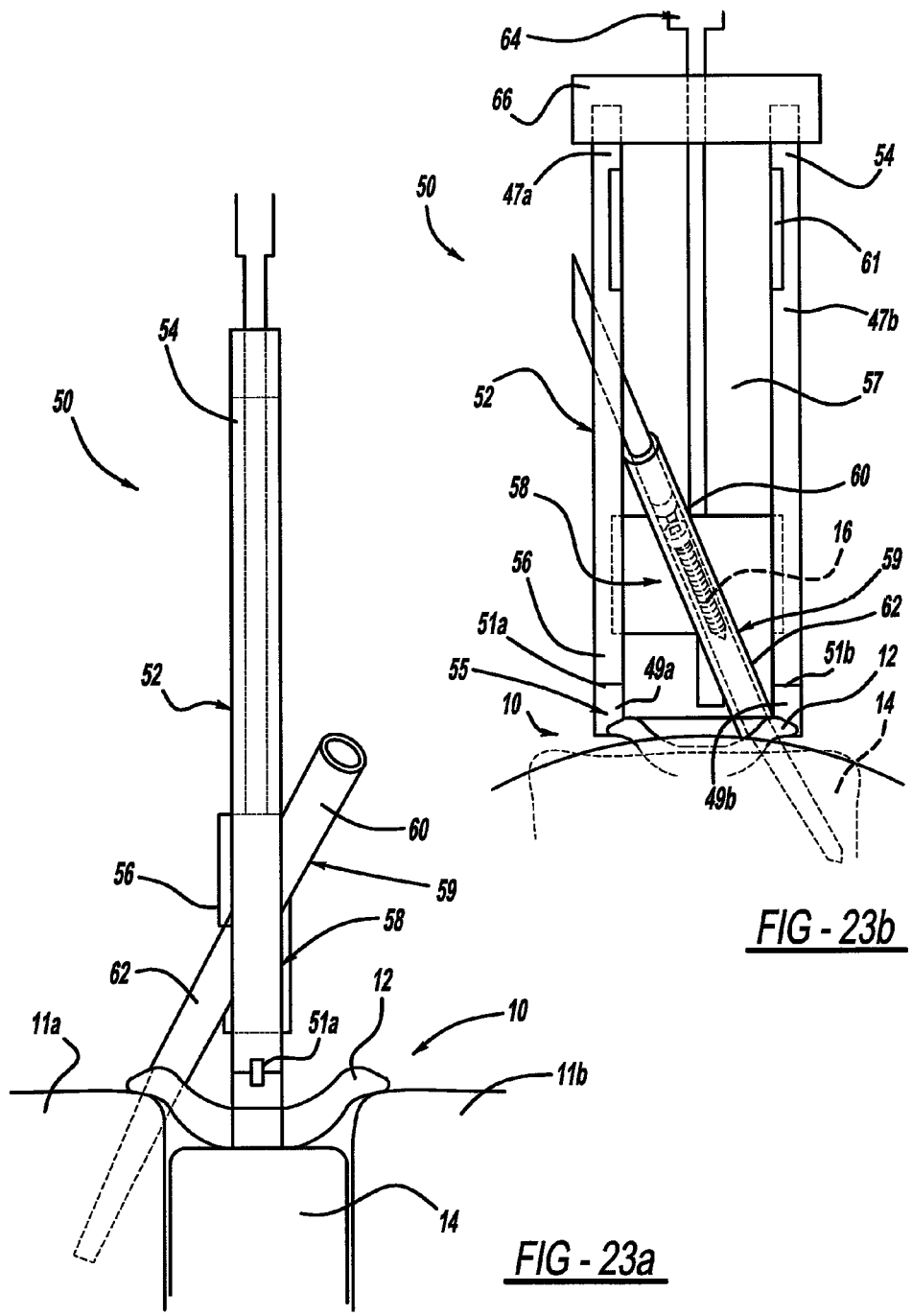

LOCKING SPINAL FUSION DEVICE

CROSS REFERENCE TO RELATED APPLICATIONS

This application claims the benefit of and priority to U.S. Provisional Application 61/240,239, filed Sep. 6, 2009, which is incorporated herein by reference.

BACKGROUND

The present disclosure relates generally to locking spinal fusion device. More specifically, the present disclosure relates to an implant to be inserted between two vertebrae that can be locked into position and form bone fusion between the two vertebrae.

Diseases of the vertebral column requiring surgical intervention are relatively common. A variety of conventional devices exist for specific areas of the vertebral column to provide restoration, decompression, or stabilization of the spine. The devices vary in size, shape, materials used, and insertion techniques. Typically these devices include an implant that is inserted in the intervertebral space defined between two adjacent vertebrae and is secured to the vertebrae via a plurality of fasteners.

While these conventional devices may generally provide adequate results, they have several disadvantages. For example, conventional devices typically use screws as fasteners to anchor the device to the vertebrae and maintain the device in position. The screws, however, are subjected to high stress forces that can cause the screws to become either partially or completely disconnected from the vertebrae. This enables the device to be relatively mobile or even completely detached and dislocated from the vertebrae. The disadvantages of conventional devices may become particularly pronounced when these conventional devices are implemented for anterior or anterolateral approaches to the spine, which can lead to exorbitant expenses, patient safety issues, supply issues, and the constant need to train and/or retrain surgeons and staff.

Thus, there is a need in the art for an easier to use, safer, more cost-effective, and more reliable spinal fusion device that can be implanted in the vertebrae of the spine and locked in position to prevent movement or detachment of the device. There is also a need in the art for a method of implanting the spinal fusion device in the spinal vertebrae.

SUMMARY

Accordingly, the present disclosure relates to a spinal fusion device for implantation between spinal vertebrae. The spinal fusion device includes a cage member having a wall with an opposed upper and lower surface, an outer side surface, and an inner side surface defining a central opening. The wall includes an aperture having internal threads for receiving a locking fastener. The spinal fusion device also includes a generally planar plate member attached to the cage member wall. The plate member includes an angled aperture for receiving an anchoring fastener and a central aperture for receiving a locking fastener. The anchoring fastener includes a head portion and a shank portion. The anchoring fastener is inserted into the angled aperture at a predetermined angle. The locking fastener includes a head portion and a shank portion. The locking fastener is inserted through the central aperture of the plate member and into the aperture of the cage member. The head portion of the locking fastener partially overlaps the head portion of the anchoring fastener to prevent the anchoring fastener from becoming displaced and lock the spinal fusion device in position.

Also provided is a method of implanting a spinal fusion device for implantation between spinal vertebrae. The method includes inserting a spinal fusion device between spinal vertebrae. An insertion guide system having a cannulated guide is then clamped onto the spinal fusion device. A plurality of holes are then into the spinal vertebrae using the cannulated guide. A plurality of anchoring fasteners are then secured into the spinal fusion device and spinal vertebrae using the cannulated guide. A locking screw is then secured into the spinal fusion device using the insertion guide to thereby lock the spinal fusion device in position.

Also provided is a guide system for implanting a spinal fusion device having a plate member and a cage member. The guide system includes an insertion guide having a first and second end, a longitudinal channel formed by a pair of opposing long arms connected to a pair of opposing short arms that form a clamp. A drill guide is slidably disposed within the longitudinal channel. The drill guide includes a cannulated guide for guiding items, such as, fasteners, drills, or the like, therethrough. A rotation device having an upper end and a lower end is coupled to the drill guide. The rotation device enables selective rotation of the drill guide so that the drill guide can be aligned with apertures located on the spinal fusion device.

One advantage of the present disclosure is that the spinal fushion device has an all-in-one system design for the treatment of a wide range of spinal conditions. Another advantage is that the spinal fusion device that can be reliably locked into position with improved retention and also detached when desired. Still another advantage is that the spinal fusion device that can be uniformly inserted from an anterior or anterolateral approach anywhere in the vertebral column for use in a variety of different spinal pathologies including degeneration, trauma, tumor, infection, or congenital abnormalities. Yet another advantage is that the spinal fusion device mitigates tissue destruction, increases surgical implant speed, has more stable biomechanical properties, enables easy reversibility, requires less equipment in an operating room to implant and/or stored in sterile containers, enables the utilization of a variety of graft configurations, and ultimately lowers costs.

Other features and advantages of the present disclosure will be readily appreciated, as the same becomes better understood after reading the subsequent description taken in conjunction with the accompanying drawings.

BRIEF DESCRIPTION OF THE DRAWINGS

FIG. 5 is an exploded perspective view of the spinal fusion device of FIG. 1, according to an exemplary embodiment.

FIG. 6 is a front view of the spinal fusion device of FIG. 1 implanted between two adjacent vertebral bodies in the anterior aspect of the lumbar spine.

FIG. 7 is a partial cross-section side view of the spinal fusion device in FIG. 6.

FIG. 8 is a front view of the spinal fusion device of FIG. 1 implanted between two adjacent vertebral bodies in the anterior aspect of the cervical spine.

FIG. 9 is a partial cross-section side view of the spinal fusion device in FIG. 8.

FIG. 14 is an exploded perspective view of a spinal fusion device having a graft lock and locking screw, according to another embodiment.

FIG. 15 is a side, top, and back view of the graft lock of the spinal fusion device of FIG. 14, according to an exemplary embodiment.

FIG. 16 is a perspective view of the screw lock of the spinal fusion device of FIG. 14, according to an exemplary embodiment.

FIG. 17 is a partial cross-section side view of the spinal fusion device in of FIG. 14 implanted between two adjacent vertebral bodies of the spine.

FIG. 18 is a partial cross-section side view of a spinal fusion device having a locking cage screw and a locking nut and the spinal fusion device implanted between adjacent vertebral bodies of the spine, according to another embodiment.

FIG. 19 is a partial cross-section top view of the spinal fusion device in FIG. 18.

FIG. 21a is a front view of a spinal fusion device inserted in between spinal vertebrae, according to an exemplary embodiment.

FIG. 21b is a side view of a guide system for implanting a spinal fusion device, according to an exemplary embodiment FIG. 21c is a side view of a guide system for implanting a spinal fusion device, according to an exemplary embodiment.

FIG. 21d is a side view of the guide system of FIG. 21c coupled to a spinal fusion device implanted between vertebrae, according to an exemplary embodiment.

FIG. 22c is a side view of a guide system coupled to a spinal fusion device implanted between vertebrae, according to an exemplary embodiment.

FIG. 22d is an enlarged side view of a spinal fusion device implanted between vertebrae with the locking screw removed, according to an exemplary embodiment.

FIG. 23a is a side view of a guide system coupled to a spinal fusion device, according to another embodiment.

FIG. 23b is a partial cross section view of the guide system of FIG. 23a, according to an exemplary embodiment.

DETAILED DESCRIPTION

Figure 1:
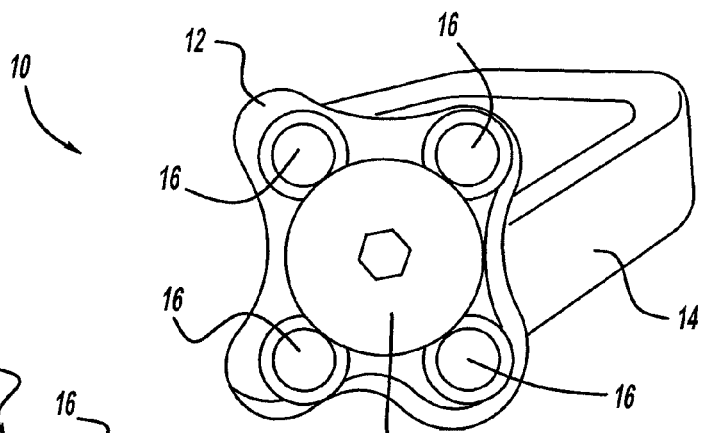
FIG. 1 is a perspective view of a spinal fusion device, according to an exemplary embodiment.
Figure 2:
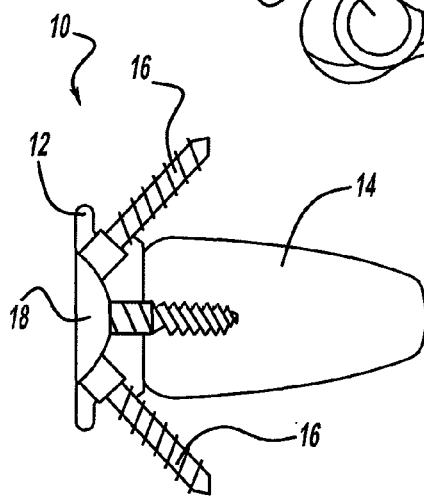
FIG. 2 is a side view of the spinal fusion device of FIG. 1, according to an exemplary embodiment.
Figure 3:
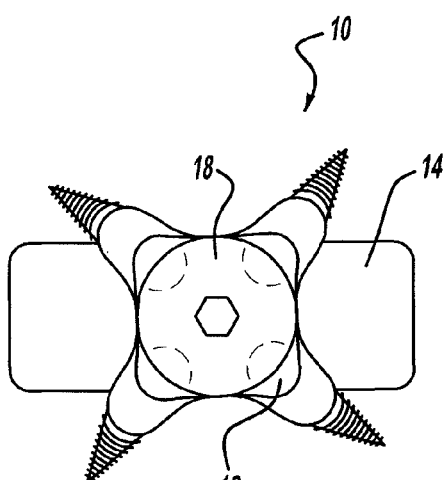
FIG. 3 is a front view of the spinal fusion device of FIG. 1, according to an exemplary embodiment.
Figure 4:
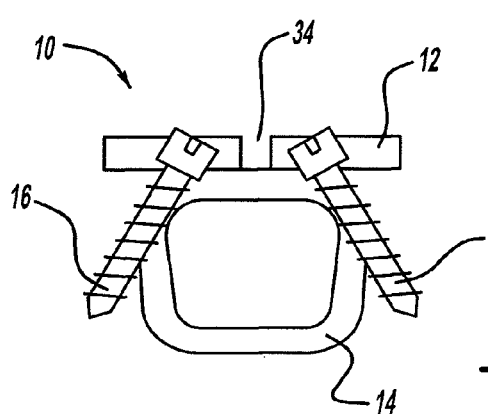
FIG. 4 is a top view of the spinal fusion device of FIG. 1, according to an exemplary embodiment.

Referring generally to the FIGURES and particularly to FIGS. 1-5, a locking spinal fusion device is shown. The locking spinal fusion device 10 is designed to be implanted in regions of the spine, such as, between adjacent vertebrae 11a, 11b in the anterior and anterolateral aspects of the cervical, thoracic, and lumbar spine. The spinal fusion device 10 includes a plate member 12, a cage/graft/implant member 14, a plurality of anchoring fasteners 16, and a locking fastener 18. The spinal fusion device 10 and the individual components can be fabricated from various materials, such as, plastic, metal, alloys, or the like, and can be magnetic resonance imaging (MRI) compatible.

The plate member 12 is generally rectangular in shape and includes a first surface 20, a second surface 22, four sides or edges 24, 26, 28, 30, and a center area 32. The sides 24, 26, 28, 39 can also be scalloped. Although the plate member 12 shown is generally rectangular in shape it can have a variety of other shapes, such as, square, circular, oval, or the like. The plate member 12 is contoured to facilitate implantation into the spine and coupling of adjacent vertebrae. For example, the plate member 12 is generally planar near the perimeter of the four side or edges 24, 26, 28, 30 to facilitate attachment to the outer surface of a vertebrae and the center area 32 of the first surface 20 is generally concave to create a depression which facilitates insertion between vertebrae. The plate member 12 includes a plurality of apertures 34 (holes, etc.) on the first and second surfaces 20, 22 for inserting the anchoring and locking fasteners 16, 18 (e.g., bolts, screws, etc.) therethrough. The apertures 34 can be threaded to receive fasteners, such as, screws, or the like. In this embodiment, there is an aperture 32 for an anchoring screw 16 located in each corner of the plate member 12 and an aperture 34 for a locking screw 18 located in the center area 32 of the plate member 12. The apertures 32, and in particular the apertures 32 for the anchoring screws 16, can be angled (e.g., diagonally, etc.) such that the anchoring screws 16 can be screwed therein divergently away from each other to strengthen attachment and performance of the device.

The cage member 14 is generally oval or ringed shape and includes an upper surface 36, a lower surface 38, an outer wall or side 40, an inner wall or side 42, and a central opening 44 (e.g., hole, aperture, etc.). Although the cage member shown is generally ringed shape it can have a variety of other shapes, such as, square, circular, oval, or the like. The cage member 14 is also contoured to facilitate implantation into the spine and coupling of adjacent vertebrae. The central opening 44 is designed to receive various materials, such as, spongy bone, bone material, or the like, and to accommodate bone growth. In this embodiment, the cage member 14 is contoured to complement the surface contours of adjacent vertebrae. The surfaces and walls of the cage member 36, 38, 40, 42 can also have a particular texture (e.g., smooth, serrated, toothed, grooved, etc.) to facilitate gripping, attachment, or the like. The cage member 14 can also have a plurality of apertures 32 that can be threaded to receive fasteners, such as, screws, or the like. In this embodiment, the cage member 14 includes an aperture 34 located on the outer front wall 40 for insertion of the locking screw 14 to thereby secure the plate member 12 to the cage member 14.

Any number of anchoring fasteners 16 and locking fasteners 18 can be used with the spinal fusion device 10. The anchoring and locking fasteners include a head portion and a shank portion. The anchoring fasteners 16 and/or locking screws can have various predetermined dimensions (e.g., length, size, shape, etc.) depending on factors, such as, the location of implantation, the purpose of implantation, or the like. The anchoring fasteners 16 can also be designed to have varying attributes along their length, such as, thread pitch, thread length, non-threaded areas or lag areas, or the like. In this embodiment, four anchoring screws 16 and one locking screw 18 is used and are completely threaded. The locking screw 18 can also have a head or top portion having a larger diameter than the head portion of the anchoring screws 16 to prevent the anchoring screws 16 from becoming detached (e.g., unscrewed, etc.) from the vertebrae, and to further secure the spinal fusion device 10 in position. The locking screw 18 can also have a head or top portion having a shape complimentary to the center area 32 of the plate member 12 (e.g., convex to match the depression, etc.).

In its assembled configuration, the cage member 14 is interposed between adjacent vertebrae. The plate member 12 is positioned on the cage member 14 such that the center area 32 of the second surface 22 of the plate member 12 is adjacent the front outer wall 40 of the cage member 14. The plate member 12 is external to and spans the vertebrae disc space. The four anchoring screws 16 attach the plate member 12 to the adjacent vertebrae. The locking screw 18 locks the plate member 12 to the cage member 14, and also locks the anchoring screws 16 in position.

Figure 10:
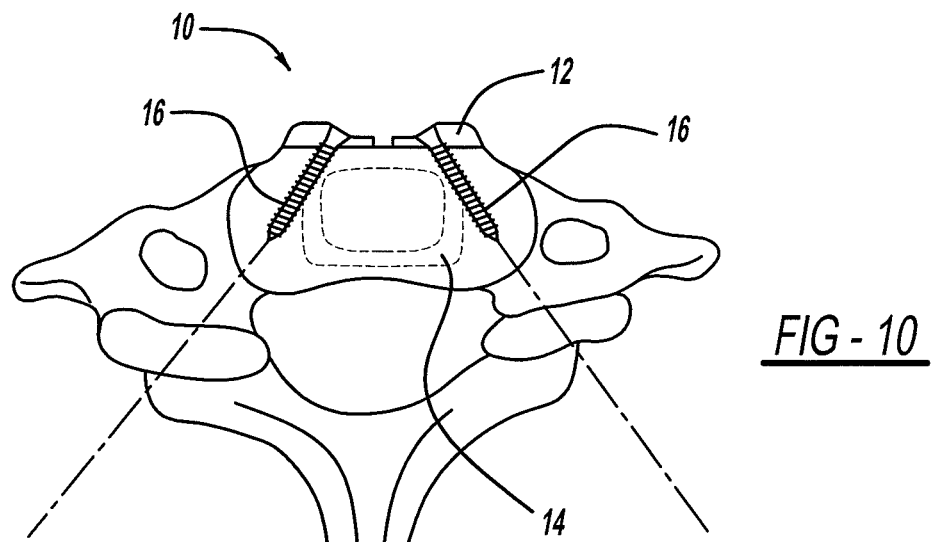
FIG. 10 is a partial cross-section top view of the spinal fusion device in FIG. 8.
Figure 11:
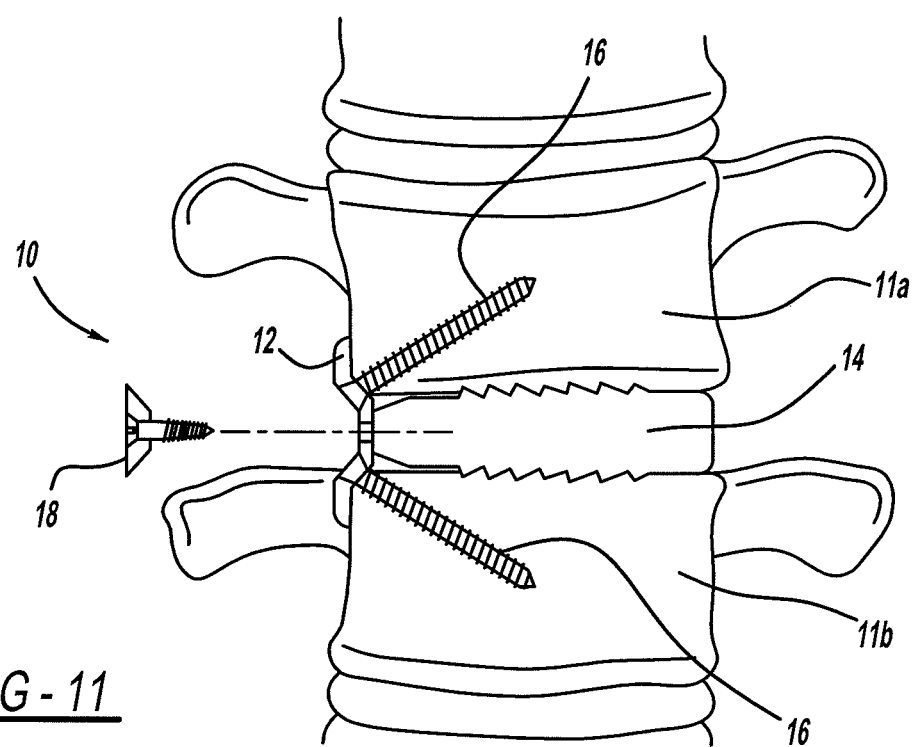
FIG. 11 is a partial cross-section side view of the spinal fusion device of FIG. 1 implanted between two adjacent vertebral bodies in the anterolateral aspect of the lumbar spine.
Figures 12, 13:
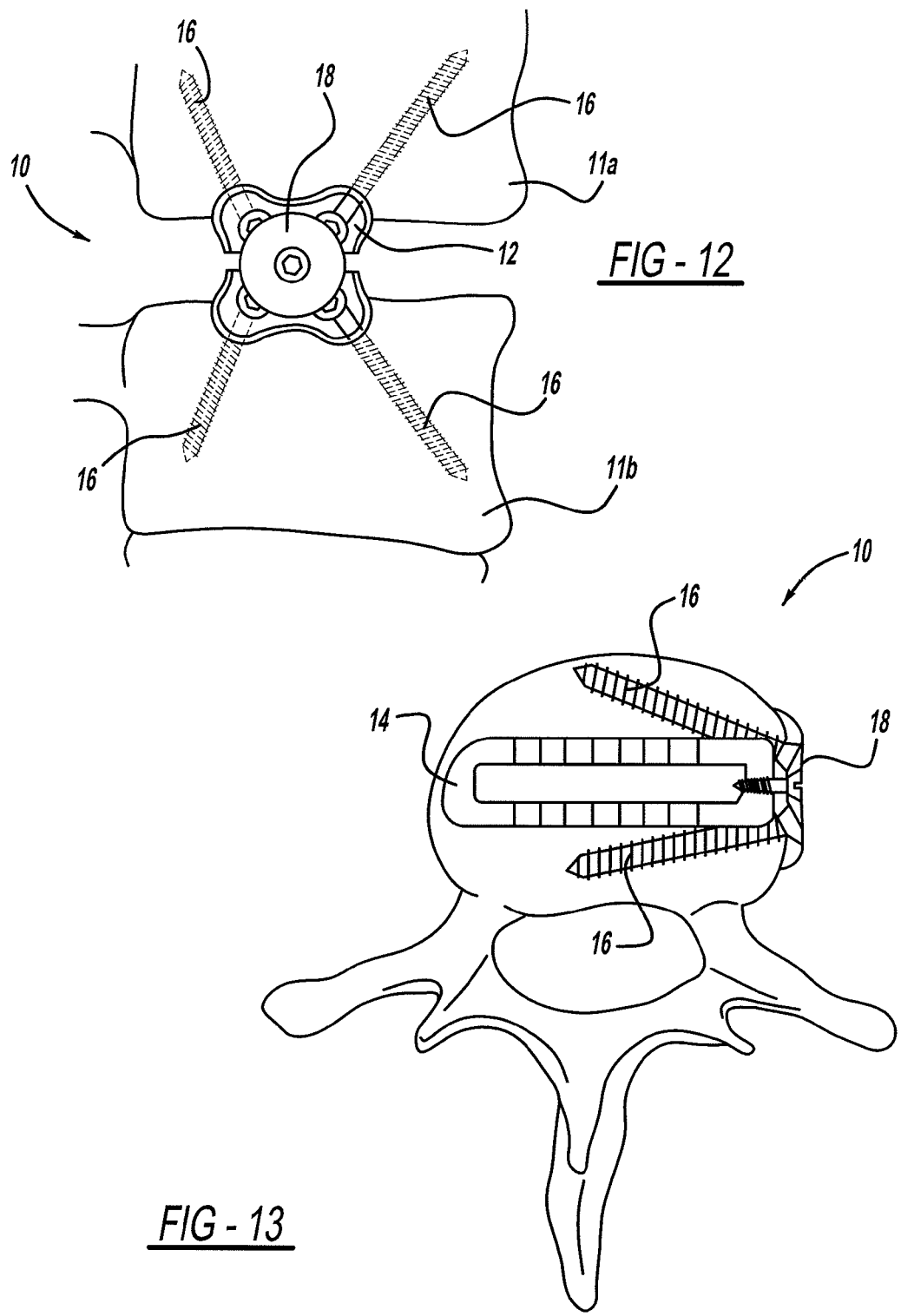
FIG. 12 is a partial cross-section front view of the spinal fusion device in FIG. 11.
FIG. 13 is a partial cross-section top view of the spinal fusion device in FIG. 11.

Referring now to FIGS. 6-13, an implanted spinal fusion device 10 is shown. The spinal fusion device 10 can be implanted in various areas of the cervical, thoracic, and lumbar spine. For example, the spinal fusion device 10 can be implanted in between two adjacent vertebral bodies in the anterior aspect of the lumbar spine, as shown in FIGS. 6-7. The spinal fusion device 10 can also be implanted between two adjacent vertebral bodies in the anterior aspect of the cervical spine, as shown in FIGS. 8-10. The spinal fusion device 10 can also be implanted between two adjacent vertebral bodies in the anterolateral aspect of the lumbar spine, as shown in FIGS. 11-13.

Referring now to FIGS. 14-17, a spinal fusion device 10 according to another embodiment is shown. In this embodiment, the spinal fusion device 10 includes a graft or cage lock 46. The cage lock 46 is generally T-shaped like a small screw having a head or top portion and a shaft. The cage lock 46 and particularly the head portion, is relatively small in size (e.g., thickness, etc.) so as not to crowd the area and hinder bone growth through the central opening 44 of the cage member 14. The shaft is tubular or hollow and includes internal threads for receiving the threaded portion of the locking screw 18. The cage lock 46 is inserted into the predrilled aperture 34 on the front wall of the cage member 14. In addition, male/female orientation is selectable depending on the application. The locking screw 18 is inserted through the plate member 12 and into the threaded shaft of the cage lock 46, pulling the plate member 12 and cage member 14 together. It should be appreciated that one or more plate members 12 may be utilized. The shaft of the locking screw 18 can have various designs. For example, in this embodiment, the shaft of the locking screw 18 includes a first threaded portion for engaging the threaded aperture 34 of the plate member 12, a lag or portion without threads, and second threaded portion for engaging the threaded shaft of the cage lock 46. The cage lock 46 provides for a stronger interface between the cage member 14 and the locking screw 18. The cage lock 46 can be inserted into the cage member 14 prior to implantation and can be used across various types and designs of cage members 14.

Referring now to FIGS. 18-19, a spinal fusion device according to another embodiment is shown. In this embodiment, the spinal fusion device 10 includes a cage lock 46 that has a relatively longer shaft having external threads, and a locking nut 48, as opposed to a locking screw 18 of the previous embodiments. The locking nut 48 includes a center aperture for receiving the threaded shaft of the cage lock 46. The threaded shaft of the cage lock 46 is inserted through the center aperture of the plate member 12 and screws into the threaded aperture of the locking nut 48.

Figure 20:
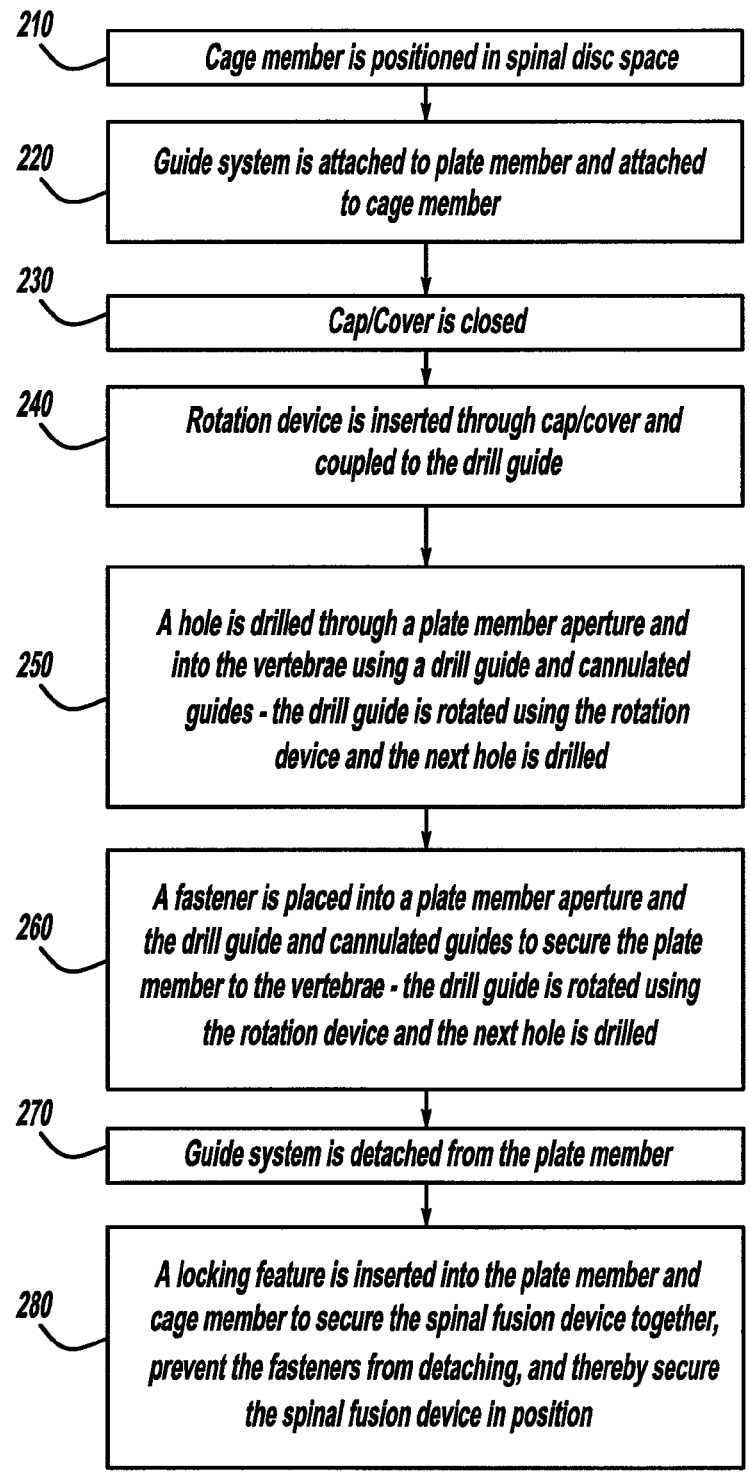
FIG. 20 is a flow chart showing a method of implanting a spinal fusion device between adjacent vertebral bodies of the spine, according to an exemplary embodiment.

Referring now to FIG. 20, a flow chart of a method of implanting a spinal fusion device 10 between adjacent vertebral bodies of the spine is shown. The method begins at block 210 and includes the step of inserting the cage member 14 of the spinal fusion device 10 between adjacent vertebrae 11a, 11b. More particularly, the cage member 14 is driven into the disc space between adjacent vertebrae, 11a, 11b. Alternatively, the plate member 12 can be pre-attached to the cage member 14 and then driven into the disc space as one unit using a guide system 50, such as, a plate clamp/screw guide, or the like, which are described in greater detail below.

The method advances to block 220 and includes the step of attaching or clamping the guide system 50 onto the spinal fusion device 10. More particularly, the plate clamp/screw guide of the guide system 50 is attached to the plate member 12 using the clamping mechanism whereby the teeth of the clamping mechanism clamp onto the edges of the plate member 12. The lateral edges of the plate member 12 are scalloped, such that the clamp teeth fit the scalloped area of the plate member 12 in that the teeth have the same curve as the scalloped area of the plate member 12. The clamp is secured to the plate member 12 by distracting the long arms of the clamp whereby the teeth and the short arms of the clamp contract thereby clasping/clamping onto the plate member 12. The fulcrum of the clamp has a unique male protrusion that marries the female curve of the surface of the plate member 12. Within the fulcrum and male protrusion is a hole which enables for a fastener (e.g., provisional screw, nut, or the like, to attach the guide system and plate member 12 to the cage member 14.

The method advances to block 230 and includes the step of closing the cap/cover 66 of the guide system 50 by pivoting the cap 66 down from one long arm of the guide 50 to the other long arm of the guide 50. The cap cover 66 enables impaction of the plate member 12 and cage member 14 as desired.

The method advances to block 240 and includes the step of inserting a rotation pin (swivel device, swivel stick) 64 through a hole located on the cap/cover 66 and attached or screwed into the drill guide 58. The swivel device includes an upper portion 65a and a lower portion 65b. Once coupled together the swivel device 64 can be used to rotate or swivel the drill guide 58 from different fastener holes 34. Cutout areas 61 in the long arms of the guide system 50 enable the drill guide 58 to be rotated within the drill guide channel 57. The long arms of the clamp have longitudinal grooves/slots on the interior side of the clamp that guide the drill guide 58 up and down to the plate member 12 for delivery of items, such as, fasteners, drill, awl, or the like. The drill guide 58 includes one or more drill guide cannulas 59.

The method advances to block 250 and includes the step of using a cannulated guide 59 to guide a device (e.g., drill, awl, etc.) through an aperture 34 of the plate member and drill a hole into the vertebrae bodies. This is repeated for each aperture 34 of the plate member 12 by rotating the drill guide into position with respect to each aperture 34.

The method advances to block 260 and includes the step of using the cannulated guide 59 to guide a fastener (e.g., screw, etc.) into the apertures and fasten the anchoring screws 16 into the holes created in the vertebrae bodies. This is repeated for each aperture 34 of the plate member 12 by rotating the drill guide 58 into position with respect to each aperture 34.

The method advances to block 270 and includes the step of detaching or unclamping the guide system 50 from the plate member 12. More particularly, the clamp of the guide system 50 is removed by detaching the cap 66 and compressing the long arms of the guide system 50.

The method advances to block 280 and includes the step of inserting a locking screw 18 into the apertures of the plate member 12 and the cage member 14 to secure the spinal fusion device 10 in position and prevent the fasteners from detaching.

Referring now to FIGS. 21a-21d, an implanted spinal fusion device 10 and a guide system 50 for implanting a spinal fusion device 10 is shown. The guide system 50 includes a K-wire 74, or the like, for guided insertion of the plate member 12 and cage member 14 into the disc space between vertebrae 11a, 11b, as shown in FIG. 21b. The K-wire 74 can also be used to drill a hole into the plate member 12 and cage member 14 and for insertion of a fastener 16, such as, a locking screw 18. The guide system 50 also includes a cannulated impactor 70 coupled to the body portion 76 of the guide system 50 which aids in implantation of the spinal fusion device 10, as shown in FIG. 21c. The guide system 50 also includes a drill guide 58 coupled to the lower end of the body 76 of the guide system 50. The drill guide 58 assists in securing the plate member 12 to the cage member 14. The cannulated impactor 70 includes a lock 72 for selectively securing the K-wire 74, drill guide 58, and guide system 50 in position, as shown in FIG. 21d.

Figures 22A, 22B:
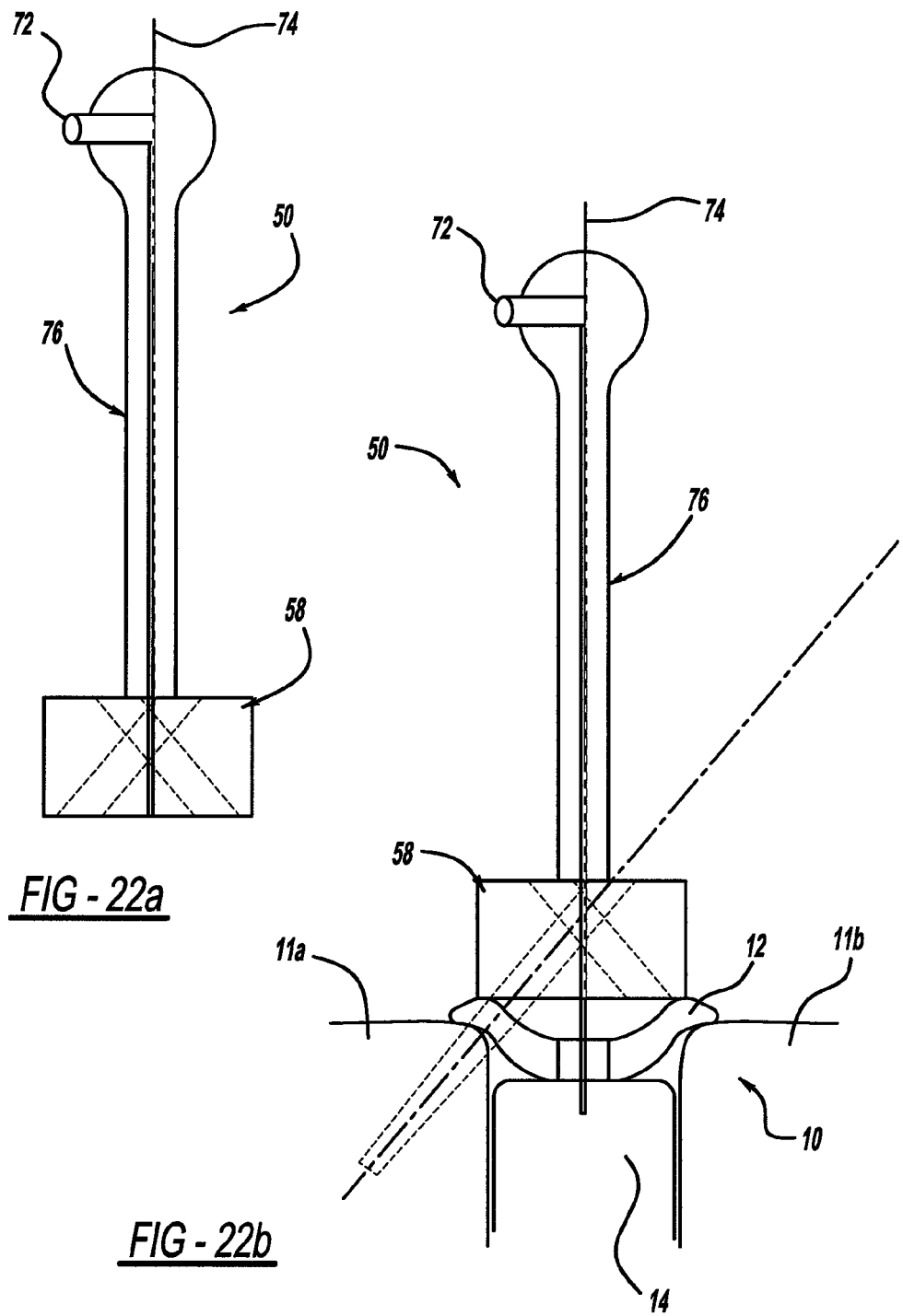
FIG. 22a is a side view of a guide system for implanting a spinal fusion device, according to another embodiment.
FIG. 22b is a side view of the guide system of FIG. 22a coupled to a spinal fusion device implanted between vertebrae, according to an exemplary embodiment.
Figure 23C:
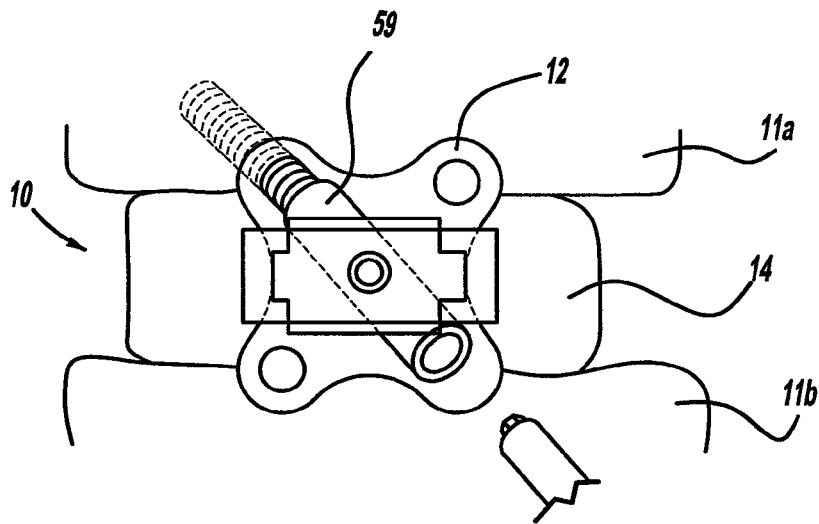
FIG. 23c is an enlarged front view of the guide system of FIG. 23a, according to an exemplary embodiment.
Figure 23D:
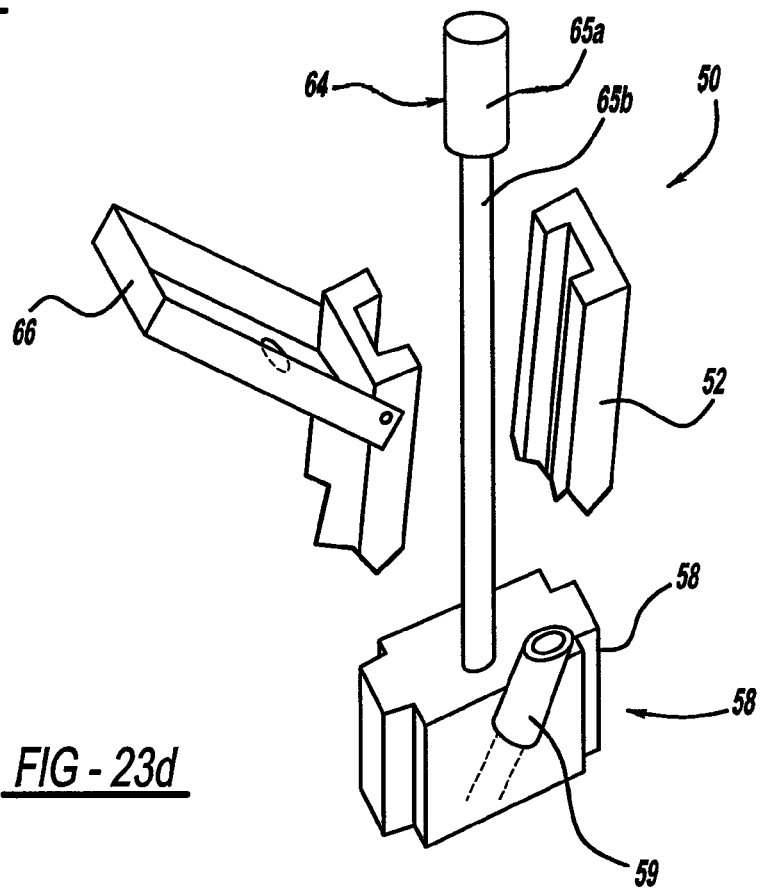
FIG. 23d is a partial exploded perspective view of the guide system of FIG. 23a, according to an exemplary embodiment.

Referring now to FIGS. 22a-22d, a guide system 50 for implanting a spinal fusion device 10 according to another embodiment is shown. In this embodiment, the guide system 50 includes a drill guide 58 having a cannulated guide 59 for guiding a device, such as, an awl, a drill, or the like, to pre-drill holes into the vertebrae 11a, 11b. The drill guide 58 is coupled to the lower end of the body 76 of the guide system 50, as shown in FIG. 22a-22b. After pre-drilling holes into the vertebrae 11a, 11b, the guide system 50 can be partially removed leaving the K-wire 74 coupled to the plate member 12 and the cage member 14 such that the anchoring fasteners 16 (screws, or the like) can be inserted into the plate member 12 and vertebrae 11a, 11b, as shown in FIG. 22c. The K-wire 74 can then be removed and used to install the locking screw 18, as shown in FIG. 22d.

Referring now to FIGS. 23a-23d, a guide system 50 for implanting a spinal fusion device 10 according to another embodiment is shown. The guide system 50 includes an insertion guide or plate clamp 52 having a first end 54 and a second end 56, and is generally tubular in shape having a pair of long arms (longitudinal arms, sides, walls, etc.) 47a, 47b, and a pair of short arms 49a, 49b (longitudinal arms, sides, walls, etc.) forming an internal channel 57. The long arms 47a, 47b and short arms 49a, 49b are connected together at hinge axes 51a, 51b. The second end of the insertion guide 52 acts as a clamp 55 and is designed to clamp to the plate member 12. This is accomplished by distracting the long arms 47a, 47b whereby the teeth and the short arms 49a, 49b of the clamp 55 contract, thereby clamping onto the plate member 12 (or "biting the plate"). The fulcrum of the clamp 55 has a unique male protrusion that marries the female curve of the surface of the plate member 12. Within the fulcrum and male protrusion is a hole which enables a fastener, such as a provisional screw or nut, to temporarily secure the guide system 50 and plate member 12 to the cage member 14. The insertion guide 52 is designed to receive a device (e.g., flexible screw driver, drill, etc.) and guide the insertion of the locking screw 18. The guide system 50 also includes a drill guide 58 having one or more cannulated guides 59 attached to the second end 56 of the insertion guide 52. The cannulated guide 59 includes a first end 60 and a second end 62, and is generally tubular in shape. The cannulated guide 59 is designed to receive a device (e.g., flexible screw driver, drill, etc.) and guide the insertion of the anchoring screws 16 into the plate member 12 and vertebrae. The guide system 50 also includes a rotation pin 64 (or swivel device) having an upper portion 65a and a lower portion 65b. The rotation pin 64 is coupled or screwed into the drill guide 58. The rotation pin 64 can be used to rotate the position of the drill guide 58 to thereby align the cannulated guides 59 with the apertures 34 of the plate member 12. The insertion guide 52 includes cutout areas 61 that enable the drill guide 58 to be rotated within the channel of the insertion guide 52. The long arms 47a, 47b, include a longitudinal slots on the interior side of the insertion guide 52 that guide the drill guide 58 up and down the channel 57 to the plate member 12 for delivery of each fastener 16 as well as other devices, such as, an awl to pre-drill fastener 16 holes 34 into the vertebrae 11a, 11b. The first end 54 of the insertion guide 52 can include a detachable cover 66 coupled thereto, such as, by a hinge or the like. The detachable cover 66 includes an aperture such that other items can be inserted there through, such as, the rotation pin 64, or the like. Once the insertion guide 52 is clamped onto the plate member 12, the cover 66 can be closed (flipped down) onto the other long arm 47b enabling impaction of the plate member 12 and cage member 14 as desired. Once the fasteners 16 are in place, the insertion guide 52 is removed by opening the cover 66 and compressing the long arms 47a, 47b. If the insertion guide 52 is utilized with a provisional fastener 16, the fastener 16 would be loosened prior to removal of the insertion guide 52. The guide system can also include and be used with other devices, such as, k-wire 74, or the like.

The present disclosure has been described in an illustrative manner. It is to be understood that the terminology which has been used is intended to be in the nature of words of description rather than of limitation.

Many modifications and variations of the present disclosure are possible in light of the above teachings. Therefore, within the scope of the appended claim, the present disclosure may be practiced other than as specifically described.

What is claimed is:

1. A spinal fusion device for implantation between spinal vertebrae, the spinal fusion device comprising:
    a cage member having a wall with opposed upper and lower surfaces, an outer side surface, and an inner side surface defining a central opening, wherein the wall includes an aperture;
    an anchoring fastener;
    a locking fastener;
    a locking member comprising a head positioned within the central opening such that the head engages the inner side surface, the locking member comprising a shaft that extends from the head and into the aperture; and a generally planar plate member attached to the outer side surface, the plate member having an inner surface that is fixed relative to a body of the plate member and defines an angled aperture for receiving the anchoring fastener, the body comprising a central aperture for receiving the locking fastener, wherein the anchoring fastener includes a head portion and a shank portion that is inserted into the angled aperture at a predetermined angle such that an outer surface of the head portion engages the inner surface, wherein the locking fastener includes a head portion and a shank portion that is inserted through the central aperture of the plate member and into the shaft such that the head portion of the locking fastener partially overlaps the head portion of the anchoring fastener to prevent the anchoring fastener from becoming displaced and lock the spinal fusion device in position, the shank portion of the locking fastener comprising first and second threaded portions that are spaced apart by an unthreaded lag portion.

2. The spinal fusion device of claim 1, wherein the shaft includes internal threads that engage external threads on the shank portion of the locking fastener.

3. The spinal fusion device of claim 2, wherein the locking fastener is inserted through the central aperture of the plate member and into the shaft of the locking member to lock the spinal fusion device in position with respect to the spinal vertebrae.

4. The spinal fusion device of claim 1, wherein a planar surface of the plate member is configured to have a contour of an adjacent spinal vertebrae.

5. The spinal fusion device of claim 1, wherein the plate member includes a concave center portion that is configured to at least partially occupy and span an internal disc space between two adjacent spinal vertebrae.

6. The spinal fusion device of claim 1, wherein the plate member includes a plurality of planar flanges that attach are configured to the outer surface of the two adjacent spinal vertebrae.

7. The spinal fusion device of claim 1, wherein the plate member includes a plurality of apertures for receiving a corresponding anchoring fastener, and each anchoring fastener is positioned to diverge away from an adjacent anchoring fastener.

8. The spinal fusion device of claim 7, wherein the anchoring fasteners diverge away from one another.

9. The spinal fusion device of claim 1, wherein the locking fastener shank portion includes a first threaded portion and a second threaded portion, and the first threaded portion has a different pitch than the pitch of the second threaded portion.

10. The spinal fusion device of claim 1, wherein the anchoring fastener shank portion includes a lag portion and a second threaded portion.

11. The spinal fusion device of claim 1, wherein the locking fastener head portion is larger than the anchoring fastener head portion.

12. The spinal fusion device of claim 1, wherein the upper and lower surfaces of the cage member have a plurality of teeth for gripping to spinal vertebrae.

13. The spinal fusion device of claim 1, wherein the head portion of the locking fastener partially overlaps the head portion of the anchoring fastener as the locking fastener is rotated 360 degrees about an axis defined by the shank portion of the locking fastener.

14. The spinal fusion device of claim 1, wherein the inner surface includes an inner thread that engages an outer thread of the anchoring fastener as the anchoring fastener is inserted into the angled aperture.

15. The spinal fusion device of claim 1, wherein the inner surface includes an inner thread that engages an outer thread of the anchoring fastener as the anchoring fastener is inserted into the angled aperture to maintain the anchoring fastener at the predetermined angle as the anchoring fastener is inserted into the angled aperture.

16. The spinal fusion device of claim 1, wherein the head portion of the anchoring fastener has a circular cross sectional configuration.

17. The spinal fusion device of claim 1, wherein the head portion of the anchoring fastener is fixed relative to the shank portion of the anchoring fastener.

18. The spinal fusion device of claim 1, wherein a second inner surface of the plate member defines the central aperture, the locking fastener being inserted through the central aperture such that an outer surface of the head portion of the locking fastener engages the second inner surface.

19. The spinal fusion device of claim 1, wherein a second inner surface of the plate member is threaded and defines the central aperture, the threaded inner surface engaging an outer thread of the locking fastener as the locking member is inserted into the central aperture.

20. The spinal fusion device of claim 1, wherein a second inner surface of the plate member is threaded and defines the central aperture, the threaded inner surface engaging an outer thread of the locking fastener as the locking fastener is inserted into the central aperture to prevent the locking fastener from pivoting relative to the plate member as the locking fastener is inserted into the central aperture.

21. The spinal fusion device of claim 1, wherein:
the inner surface includes an inner thread that engages an outer thread of the anchoring fastener as the anchoring fastener is inserted into the angled aperture to maintain the anchoring fastener at the predetermined angle as the anchoring fastener is inserted into the angled aperture; and
a second inner surface of the plate member is threaded and defines the central aperture, the threaded inner surface engaging an outer thread of the locking fastener as the locking fastener is inserted into the central aperture to prevent the locking fastener from pivoting relative to the plate member as the locking fastener is inserted into the central aperture.

22. A method comprising:
inserting the spinal fusion device recited in claim 1 between spinal vertebrae, wherein the angled aperture includes a plurality of angled apertures and the anchoring fastener includes a plurality of anchoring fasteners;
clamping an insertion guide system having a cannulated guide onto the spinal fusion device;
drilling a plurality of holes into the spinal vertebrae using the cannulated guide;
securing the plurality of anchoring fasteners into the spinal fusion device and spinal vertebrae using the cannulated guide; and
securing the locking fastener into the spinal fusion device using the insertion guide to lock the spinal fusion device in position.

23. A spinal fusion device for implantation between spinal vertebrae, the spinal fusion device comprising:
a cage member having a wall with opposed upper and lower surfaces, an outer side surface, and an inner side surface defining a central opening, wherein the wall includes an aperture, and the cage member includes a slot that engages an insertion guide;

a locking member comprising a head positioned within the central opening such that the head engages the inner side surface, the locking member comprising a shaft that extends from the head and into the aperture;

a generally planar plate member attached to the outer side surface, the plate member having a first inner surface that is fixed relative to a body of the plate member and defines an angled aperture and a second inner surface defining a central aperture, wherein the plate member includes a concave center portion that is configured to at least partially occupy and span an internal disc space between two adjacent spinal vertebrae;

an anchoring fastener including a head portion and a shank portion, the anchoring fastener being inserted into the angled aperture of the plate member at a predetermined angle such that an outer surface of the head portion engages the first inner surface; and a locking fastener including head portion and a shank portion that is inserted through the central aperture of the plate member and into the shaft, the head portion of the locking fastener partially overlapping the head portion of the anchoring fastener to prevent the anchoring fastener from becoming displaced and lock the spinal fusion device in position, the shank portion of the locking fastener comprising first and second threaded portions that are spaced apart by an unthreaded lag portion.

24. A spinal fusion device for implantation between spinal vertebrae, the spinal fusion device comprising:

a cage member having a wall with opposed upper and lower surfaces, an outer side surface, and an inner side surface defining a central opening, wherein the wall includes an aperture;

an anchoring fastener;

a locking fastener;

a locking member comprising a head positioned within the central opening such that the head engages the inner side surface, the locking member comprising a shaft that extends from the head and into the aperture; and a generally planar plate member attached to the outer side surface, the plate member having an angled aperture for receiving the anchoring fastener, a central aperture for receiving the locking fastener, wherein the anchoring fastener includes a head portion and a shank portion, and the anchoring fastener is inserted into the angled aperture at a predetermined angle, and the locking fastener includes a head portion and a shank portion that is inserted through the central aperture of the plate member and into the shaft such that the head portion of the locking fastener partially overlaps the head portion of the anchoring fastener as the locking fastener is rotated 360 degrees about an axis defined by the shank portion of the locking fastener to prevent the anchoring fastener from becoming displaced and lock the spinal fusion device in position, the shank portion of the locking fastener comprising first and second threaded portions that are spaced apart by an unthreaded lag portion.

25. A spinal fusion device for implantation between spinal vertebrae, the spinal fusion device comprising:

a cage member having a wall with opposed upper and lower surfaces, an outer side surface, and an inner side surface defining a central opening, wherein the wall includes an aperture;

an anchoring fastener;

a locking fastener;

a locking member comprising a head positioned within the central opening such that the head engages the inner side surface, the locking member comprising a shaft that extends from the head and into the aperture; and a generally planar plate member attached to the cage member wall, the plate member having a threaded inner surface defining an angled aperture for receiving the anchoring fastener, a central aperture for receiving the locking fastener, wherein the anchoring fastener includes a head portion and a shank portion, and the anchoring fastener is inserted into the angled aperture at a predetermined angle such that a threaded outer surface of the anchoring fastener engages the threaded inner surface as the anchoring fastener is inserted into the angled aperture to maintain the anchoring fastener at the predetermined angle as the anchoring fastener is inserted into the angled aperture, wherein the locking fastener includes a head portion and a shank portion that is inserted through the central aperture of the plate member and into the shaft such that the head portion of the locking fastener partially overlaps the head portion of the anchoring fastener to prevent the anchoring fastener from becoming displaced and lock the spinal fusion device in position, the shank portion of the locking fastener comprising first and second threaded portions that are spaced apart by an unthreaded lag portion.

26. The spinal fusion device of claim 25, wherein the head portion of the locking fastener partially overlaps the head portion of the anchoring fastener as the locking fastener is rotated 360 degrees about an axis defined by the shank portion of the locking fastener.

27. The spinal fusion device of claim 25, wherein the head portion of the anchoring fastener has a circular cross sectional configuration.

28. The spinal fusion device of claim 25, wherein a second inner surface of the plate member is threaded and defines the central aperture, the threaded inner surface engaging an outer thread of the locking fastener as the locking fastener is inserted into the central aperture to prevent the locking fastener from pivoting relative to the plate member as the locking fastener is inserted into the central aperture.

* * * * *

UNITED STATES PATENT AND TRADEMARK OFFICE
CERTIFICATE OF CORRECTION

PATENT NO.         : 9,730,804 B2
APPLICATION NO.    : 13/383667
DATED              : August 15, 2017
INVENTOR(S)        : Cowan, Jr. et al.

It is certified that error appears in the above-identified patent and that said Letters Patent is hereby corrected as shown below:

In the Specification

In Column 2, Line 29, delete "fushion" and insert -- fusion --, therefor.

In Column 3, Line 27, delete "in of" and insert -- of --, therefor.

In Column 3, Lines 43-44, delete "embodiment" and insert -- embodiment. --, therefor.

In Column 4, Line 37, delete "aperture 32" and insert -- aperture 34 --, therefor.

In Column 4, Line 40, delete "apertures 32," and insert -- apertures 34, --, therefor.

In Column 4, Line 41, delete "apertures 32" and insert -- apertures 34 --, therefor.

In Column 4, Line 62, delete "apertures 32" and insert -- apertures 34 --, therefor.

In Column 4, Lines 65-66, delete "locking screw 14" and insert -- locking screw 18 --, therefor.

In Column 6, Line 43, delete "like," and insert -- like), --, therefor.

Signed and Sealed this
Fourteenth Day of November, 2017

Joseph Matal
*Performing the Functions and Duties of the*
*Under Secretary of Commerce for Intellectual Property and*
*Director of the United States Patent and Trademark Office*